(12) United States Patent
Ting et al.

(10) Patent No.: US 6,730,321 B2
(45) Date of Patent: *May 4, 2004

(54) PRESS COATED, PULSATILE DRUG DELIVERY SYSTEM SUITABLE FOR ORAL ADMINISTRATION (75) Inventors: Richard Ting, Danville, CA (US); Charles Hsiao, Livermore, CA (US)

(73) Assignee: Impax Pharmaceuticals, Inc., Hayward, CA (US)

(*) Notice: Subject to any disclaimer, the term of this patent is extended or adjusted under 35 U.S.C. 154(b) by 72 days.

This patent is subject to a terminal disclaimer.

(21) Appl. No.: 10/122,410

(22) Filed: Apr. 16, 2002

(65) Prior Publication Data

US 2002/0164371 A1 Nov. 7, 2002

Related U.S. Application Data

(63) Continuation-in-part of application No. 09/053,491, filed on Apr. 2, 1998, now Pat. No. 6,372,254.

(51) Int. Cl.[7] .......................... A61K 9/24; A61K 9/20; A61K 9/22; A61K 9/28; A61K 9/30
(52) U.S. Cl. .................. 424/473; 424/464; 424/468; 424/471; 424/472; 424/474; 424/475
(58) Field of Search ................. 424/464, 468, 424/471, 472, 473, 474, 475

(56) References Cited

U.S. PATENT DOCUMENTS

| 4,242,867 A | | 1/1981 | Belart .................... 424/473 |
| 4,894,240 A | | 1/1990 | Geoghegan et al. ........ 424/497 |
| 4,971,805 A | * | 11/1990 | Kitanishi et al. ........... 424/494 |
| 5,032,406 A | | 7/1991 | Danser et al. .............. 424/472 |
| 5,162,117 A | | 11/1992 | Stupak et al. |
| 5,229,131 A | | 7/1993 | Amidometin ................ 424/451 |
| 5,238,686 A | * | 8/1993 | Eichel et al. ................ 424/461 |
| 5,334,372 A | | 8/1994 | Kawamata et al. |
| 5,374,759 A | | 12/1994 | Imperante et al. |
| 5,407,687 A | | 4/1995 | Coffin et al. ................ 424/472 |
| 5,439,689 A | | 8/1995 | Hendrickson et al. ....... 424/490 |
| 5,445,829 A | | 8/1995 | Paradissis et al. .......... 424/480 |
| 5,464,633 A | * | 11/1995 | Conte et al. ................ 424/480 |
| 5,472,708 A | | 12/1995 | Chen ......................... 424/451 |
| 5,472,711 A | | 12/1995 | Baichwal .................... 424/468 |
| 5,500,227 A | | 3/1996 | Oshlack et al. ............. 424/476 |
| 5,576,022 A | | 11/1996 | Yang et al. ................. 424/472 |
| 5,840,329 A | | 11/1998 | Fbai .......................... 424/458 |
| 6,024,976 A | * | 2/2000 | Miranda et al. ............. 424/449 |

OTHER PUBLICATIONS

USP 23: Physical Tests <724> Drug Release, pp. 1793–1799, 2534–2536, 2709–2715, 3012–3017, 3209–3215, 3468–3474.
USP 23: Nutritional Supplements<2040> Disintegration and Dissolution of Nutritional Supplements, pp. 2184–2185, 2577–2578, 2833–2834, 3794–3795.
Chem. Abs. 67: 78733 (1967).
USP 23: Physical Tests <711> Dissolution, pp. 1791–1793, 3208–3209.

* cited by examiner

Primary Examiner—Thurman K. Page
Assistant Examiner—S. Tran
(74) Attorney, Agent, or Firm—Fleshner & Kim, LLP (57) ABSTRACT

A press-coated tablet suitable for oral administration, comprising an immediate-release compartment comprising a compressed blend of an active agent. The immediate-release compartment has a dissolution profile in which 10–75% of the active agent is dissolved within one hour and not less than 90% of the active agent is dissolved within 6 hours. The tablet further comprises an extended-release compartment with a dissolution profile in which 5–40% of the active agent is dissolved within one hour, 20–75% within three hours, 40–95% of the active agent within 6 hours, and not less than 60% of the active agent is dissolved within 8 hours. Additionally, the press-coated extended-release compartment substantially envelops the immediate-release compartment, and comprises a compressed blend of the active agent, a hydrophilic polymer and hydrophobic material. The tablet exhibits a first order release of the active agent interrupted by a pulsed delivery of the active agent.

20 Claims, 4 Drawing Sheets

Immediate-Release Compartment

Extended-Release Compartment

IN-VITRO DISSOLUTION STUDY

FIGURE 4

IN-VITRO DISSOLUTION STUDY

PRESS COATED, PULSATILE DRUG DELIVERY SYSTEM SUITABLE FOR ORAL ADMINISTRATION

This is a Continuation-in-Part of application Ser. No. 09/053,491 filed Apr. 2, 1998 now U.S. Pat. No. 6,372,254. The disclosure of the prior applications is here incorporated by reference herein in its entirety.

FIELD OF THE INVENTION

The present invention pertains to a drug delivery system suitable for oral administration that facilitates a pulsatile release of the active agent. A key aspect of the present invention is the discovery that a tablet with an immediate-release compartment, which contains a compressed blend of an active agent and one or more polymers, substantially enveloped by an extended-release compartment, which contains a compressed blend of the active agent and hydrophilic and hydrophobic polymers, can provide a substantially first order delivery of the active agent, interrupted by a timed, pulsed delivery of a preferably increased amount of the active agent. With respect to drugs subject to "first pass" clearance, sustained drug delivery can be achieved through the present invention via an optional instant-release compartment, which provides a dose sufficient to exceed the liver's metabolic capacity and to maintain therapeutic levels, preferably throughout a 24-hour period.

BACKGROUND OF THE INVENTION

Drug efficacy generally depends upon the ability of the drug to reach its target in sufficient quantity to maintain therapeutic levels for the desired time period. The pulsatile release of an active agent is desirable when treating diseases that require drug delivery in a manner to maintain therapeutic levels notwithstanding circadian rhythms. Diseases that benefit from pulsatile drug delivery include angina, for example, which occurs with repeatable regularity at the end of the night and in the early morning hours while the patient is still asleep, and rheumatic diseases such as rheumatoid arthritis, the symptoms of which manifest during the night and into the beginning of the next day.

With traditional extended-release dosage formulations, which exhibit first order release rates, the efficacy of the active agent diminishes at the end of the night and the beginning of the next day. Therefore, a bolus or burst delivery of the active agent during this waning period can improve drug efficacy.

In addition, orally administered drugs must overcome several obstacles to reach their desired targets. Before orally administered drugs enter the general circulation of the human body, they are absorbed into the capillaries and veins of the upper gastrointestinal tract and are transported by the portal vein to the liver. The pH and enzymatic activities found in gastrointestinal fluids may inactivate the drug or cause the drug to dissolve poorly. Following their absorption in the intestine, certain orally administered drugs can be subject to a "first pass"clearance by the liver and excreted into bile or converted into pharmacologically inactive metabolites. Decreased bioavailability of orally administered drugs can be a consequence of this first pass effect. A first pass effect is characterized by the liver removing a drug from the bloodstream prior to entering a patient's general circulation. A drug can overcome a first pass if it is present in a sufficient quantity which exceeds the excretory or metabolic capability of the liver.

Orally administered drugs subject to the first pass effect generally exhibit nonlinear pharmacokinetics. Until the liver's metabolic capacity has been exceeded, the amount of such drugs in the bloodstream is significantly lower than the amount administered. This metabolic elimination of the given dose results in reduced bioavailability. However, once the administered dose exceeds the liver's metabolic capacity, a significant increase in the drug concentration in the bloodstream may be obtained. The first pass phenomenon presents particular difficulties in the maintenance of therapeutic levels of an orally administered drug over an extended period such as 12 or 24 hours.

Drug delivery systems that have evolved with respect to orally administered drugs subject to the first pass effect include formulations capable of immediate drug release that are suitable for administration from 3–4 times daily, and formulations capable of immediate and sustained drug release that are suitable for once-daily administration. The second type of formulation is preferred because patient compliance with prescribed drug regimens involving once-daily administration is substantially higher than those involving multiple administrations. A sustained release formulation, however, may subject the patient to toxic drug levels over part of the dosing period and sub-therapeutic drug levels over other portions of the dosing period, if the drug release does not occur at appropriate time intervals. The maintenance of therapeutic levels of an orally administered drug over an extended period thus depends upon a drug delivery system capable of providing an appropriate release pattern.

A valuable contribution to the art therefore would be the development of a drug delivery system in a single tablet formulation suitable for oral administration that facilitates a substantially first order delivery of the active agent, interrupted by a timed, pulsed delivery of a preferably increased amount of the active agent, and where the active agent is subject to "first pass" clearance, can provide sustained drug delivery, preferably over a 24-hour period, by a dose sufficient to exceed the liver's metabolic capacity and to maintain therapeutic levels.

SUMMARY OF THE INVENTION

Accordingly, an objective of the present invention is a single orally administrable tablet that can provide a substantially first order delivery of the active agent, interrupted by a timed, pulsed delivery of an increased amount of the active agent. A second objective of the present invention is a single orally administrable tablet that can overcome the "first pass" effect by providing an instant-release dosage sufficient to exceed the liver's metabolic capacity, and then continue to maintain therapeutic drug levels, preferably over a 24-hour period. A further objective of the present invention is a method for preparing a single orally administrable tablet that can provide a substantially first order delivery of the active agent, interrupted by a timed, pulsed delivery of a preferably increased amount of the active agent.

In a preferred embodiment of the invention, these and other objectives can be accomplished through a drug delivery system suitable for oral administration with an immediate-release compartment, which contains a compressed blend of an active agent and one or more polymers, substantially enveloped by an extended-release compartment, which contains a compressed blend of the active agent and hydrophilic and hydrophobic polymers, and substantially enveloped by an optional instant-release compartment, which provides a dose sufficient to exceed the liver's metabolic capacity and to maintain therapeutic levels, preferably throughout a 24-hour period.

In a preferred embodiment of the present invention, the active agent in the extended-release compartment can diffuse out first, resulting in a first order release rate. As the active agent and soluble polymers in the extended-release compartment disintegrate, water will penetrate through the extended-release compartment and cause the immediate-release compartment to expand, creating a bursting effect that further disrupts any remaining integrity of the extended-release compartment. Where an optional inert core (i.e., a core containing one or more polymers without active agent) is present, its swelling in response to the water influx described above can also contribute to a bursting effect. The respective time periods for the dissolution of the active agent, and the bursting effect, can be regulated by varying the composition and relative amounts of the polymers in the compartments.

The extended-release compartment preferably comprises a combination of hydrophilic and hydrophobic polymers. In this embodiment, once administered, the hydrophilic polymer dissolves away to weaken the structure of the extended-release compartment, and the hydrophobic polymer retards the water penetration and helps to maintain the shape of the drug delivery system. The immediate-release compartment preferably comprises a compressed blend of active agent and one or more polymers with disintegration characteristics, which upon exposure to the aqueous medium, would burst to further break apart the already weakened extended-release compartment and provide preferably complete drug release. In another embodiment, the immediate-release drug compartment and the combination of hydrophilic and hydrophobic polymers in the extended-release drug compartment can be modified so the second peak does not result in a burst. Instead, the second peak can be tailored to be completed in a desired time interval, for example, 30 minutes to 12 hours after release of active agent from the extended-release compartment.

In another embodiment, the extended-release compartment can be inert (i.e., containing a combination of hydrophilic and hydrophobic polymers without active agent), which may be preferable where delayed drug release is necessary or convenient. For example, if orally administered before bedtime, this drug delivery system could deliver its active agent while the patient is asleep to facilitate optimal therapeutic drug levels just prior to awakening.

In a preferred embodiment, the active agent is a drug, which may be a therapeutic drug or a prophylactic drug. In another preferred embodiment, the drug can be diltiazem, trapidil, urapidil, benziodarone, dipyridamole, isosorbide mononitrate, or lidoflazine. In yet another, the drug can be a non-steroidal antiinflammatory drug (NSAID) or a steroidal antiinflammatory drugs, which includes diclofenac sodium, ibuprofen, ketoprofen, diflunisal, piroxicam, motrin, and naproxen.

In still another preferred embodiment, the active agent can be one or more drugs selected from acetaminophen, aldosterone, alprenolol, amitryptyline, aspirin, beclomethasone, diproprionate, bromocriptine, bupropion, butorphanol tartrate, carbidopa, cetirizine, chlormethiazole, chlorpheniramine, chlorpromazine HCl, cimetidine, clarithromycin, codeine, cortisone, cyclobenzamine HCl, desmethylimipramine, dextropropoxyphene, dihydroergotamine, diltiazem FIG, dobutamine HCl, divalproex sodium, domperidone, dopamine HCl, doxazosine, doxepin HCl, epinephrine, ergoloid mesylates, ergotamine tartrate estradiol, ethinylestradiol, fenofibrate, fexofenadine, flunisolide, fluorouracil, flurazepam HCl, 5-fluoro-21-deoxyuridine, furosemide, glipizide, glyburide, glyceryl trinitrate, guanethidine sulfate, hydralazine HCl, imipramine HCl, indoramin, isoethorine HCl, isoethrine mesylate, isoprenaline, isoproterenol sulfate, isosorbide dinitrate, levallorphan tartrate, levodopa, lidocaine HCl, lignocaine, loratadine, lorcainide, meperidine FIG, 6-mercaptopurine, metaproterenol sulfate, mesalamine, metformin, methoxamine HCl, methylphenidate, methylpreonisolone, methyltestosterone mesylate, metoclopramide, metoprolol tartrate, metoprolol succinate, morphine sulfate, nalbuphine HCl, naloxone HCl, neostigmine, nifedipine, nitrendipine, nitroglycerin, norepinephrine bitartrate, norethindrone, nortriptylene HCl, oxprenolol, omeprazole, oxybutanin, oxycodone, oxyphenbutazone, paroxetine, penicillamine, pentazocine HCl, pentazocine lactate, pentobarbital, petnidine, phenacetin, phentolamine HCl, phentolamine mesydate, phenylephrine HCl, phenylephrine bitartrate, phenytoin, pindolal, prazosin, prednisone, progesterone, propoxyphene HCl, propoxyphene napsylate, propranolol FIG, quinidine, riluzole, reserpine, ritodrine HCl, salicylamide, salbutamol, secobarbital, testosterone, terbutaline, timolol maleate, tolbutamide, venlafaxine or verapamil HCl. The active agent which may be used in the present invention also includes those listed in U.S. Pat. No. 6,024,976, issued Feb. 15, 2000, to Miranda et al.

In another preferred embodiment, the active agent can be isosorbide-5-mononitrate.

In a preferred embodiment, the active agent of the drug delivery can exhibit the following in vitro dissolution profile when measured in a type 2 dissolution apparatus (paddle) according to U.S. Pharmacopeia XXII at 37° C. in deionized water at 75 rotations per minute:

(a) from about 0% to about 90% of said active agent is released between 1 hour and 16 hours of measurement in said apparatus; and (b) from about 0% to about 100% of said active agent is released between 1.5 hours and 28 hours after measurement in said apparatus.

In another preferred embodiment, the active agent of the drug delivery system can exhibit the following in vitro dissolution profile when measured under the same conditions described above:

(a) from about 10% to about 75% of said active agent is released between 1 hour and 5 hours of measurement in said apparatus; and (b) no less than about 90% of said active agent is released after 6 hours of measurement in said apparatus.

In yet another preferred embodiment, the active agent of the drug delivery system exhibits the following in vitro dissolution profile when measured under the same conditions described above:

(a) from about 0% to about 50% of said active agent is released after 1 hour of measurement in said apparatus;

(b) from about 0% to about 90% of said active agent is released between 1 hour and 16 hours after measurement in said apparatus; and (c) from about 0% to about 100% of said active agent is released between 1.5 hours and 28 hours after measurement in said apparatus.

In still another preferred embodiment, the active agent of the drug delivery system exhibits the following in vitro dissolution profile when measured under the same conditions described above:

(a) from about 0% to about 35% of said active agent is released after 1 hour of measurement in said apparatus;

(b) from about 10% to about 90%0 of said active agent is released between 1 hour and 5 hours after measurement in said apparatus; and (c) no less than 90% of said active agent is released after 6 hours of measurement in said apparatus.

In a preferred embodiment, the active agent exhibiting these dissolution profiles can be isosorbide-5-mononitrate.

The polymers of the drug delivery system can be one or more polymers selected from alginic acid, carboxymethylcellulose calcium, carboxymethylcellulose sodium, colloidal silicon dioxide, croscarmellose sodium, crospovidone, guar gum, magnesium aluminum silicate, magnesium stearate, methylcellulose, microcrystalline cellulose, polacrilin potassium, powdered cellulose, pregelatinized starch, sodium alginate, sodium starch glycolate, starch, ethylcellulose, gelatin, hydroxyethyl cellulose, hydroxypropyl cellulose, hydroxypropyl methylcellulose, polymethacrylates, povidone, shellac, or zein, of which colloidal silicon dioxide, croscarmellose sodium, magnesium stearate, microcrystalline cellulose, and hydroxypropyl methylcellulose are the most preferred.

The hydrophilic polymer can be any hydrophobic polymer which will achieve the goals of the present invention including, but not limited to, one or more polymers selected from carboxymethylcellulose, guar gum, hydroxyethyl cellulose, hydroxypropyl cellulose, hydroxypropyl methylcellulose, methylcellulose, or povidone, of which hydroxypropyl methylcellulose is further preferred.

The hydrophobic polymer of the drug delivery system can be any hydrophobic polymer which will achieve the goals of the present invention including, but not limited to, one or more polymers selected from carbomer, carnauba wax, ethylcellulose, glyceryl palmitostearate, hydrogenated castor oil, hydrogenated vegetable oil type 1, microcrystalline wax, polacrilin potassium, polymethacrylates, or stearic acid, of which hydrogenated vegetable oil type 1 is further preferred.

The present invention also accomplishes these and other objectives through a method for preparing a press coated, pulsatile drug delivery system suitable for oral administration including the steps of combining an effective amount of an active agent, or a pharmaceutically acceptable salt thereof, and a polymer to form an immediate-release compartment; combining an effective amount of an active agent, or a pharmaceutically acceptable salt thereof, and a combination of hydrophilic and hydrophobic polymers to form an extended-release compartment; and press coating the extended-release compartment to substantially envelop the immediate-release compartment.

A preferred embodiment further includes the steps of combining an effective amount of an active agent, or a pharmaceutically acceptable salt thereof, and a polymer to form an instant-release compartment, and press coating the instant-release compartment to substantially envelop the extended-release compartment.

In another preferred embodiment, the combining steps can be done by blending, wet granulation, fluid-bed granulation, or dry granulation according to methods recognized the art.

Other objects, features and advantages of the present invention will become apparent from the following detailed description. The detailed description and the specific examples, however, indicate only preferred embodiments of the invention.

Various changes and modifications within the spirit and scope of the invention will become apparent to those skilled in the art from this detailed description.

DESCRIPTION OF DRAWINGS

| Time (minutes) | Mean Percent Dissolved | Standard deviation (n = 12) |
|---|---|---|
| 0 | 0 | 0 |
| 30 | 11.3 | 0.4 |
| 60 | 17.1 | 0.6 |
| 120 | 25.7 | 1.2 |
| 180 | 32.1 | 1.6 |
| 240 | 55.8 | 21.6 |
| 300 | 90.9 | 11.0 |
| 330 | 95.6 | 4.8 |
| 360 | 97.5 | 4.1 |
| 420 | 98.8 | 4.2 |
| 480 | 98.9 | 4.5 |
| 540 | 99.0 | 4.6 |
| 600 | 98.3 | 4.8 |

| Time (minutes) | Percent Dissolved | Standard deviation |
|---|---|---|
| 0 | 0 | 0 |
| 30 | 20.2 | 0.8 |
| 60 | 23.3 | 0.8 |
| 120 | 27.8 | 0.8 |
| 180 | 31.4 | 0.9 |
| 240 | 35.2 | 1.5 |
| 300 | 74.4 | 25.8 |
| 330 | 91.4 | 4.8 |
| 360 | 94.2 | 2.4 |
| 420 | 95.6 | 1.6 |
| 480 | 96.1 | 1.6 |
| 540 | 96.2 | 1.4 |

DESCRIPTION OF PREFERRED EMBODIMENTS

Figure 1:
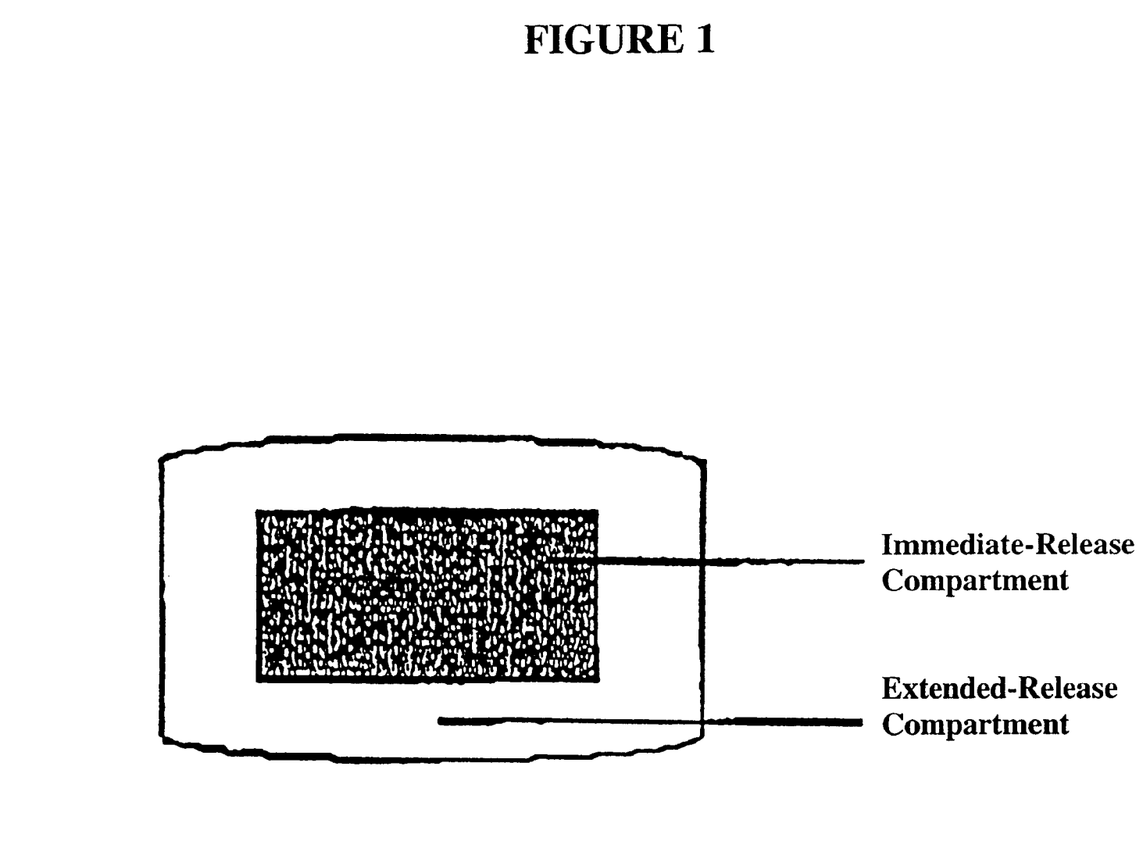
FIG. 1. is a schematic of a press coated, pulsatile drug delivery system of the present invention suitable for oral administration with an immediate-release compartment, which contains a compressed blend of an active agent and one or more polymers, substantially enveloped by an extended-release compartment, which contains a compressed blend of the active agent and hydrophilic and hydrophobic polymers.
Figure 2:
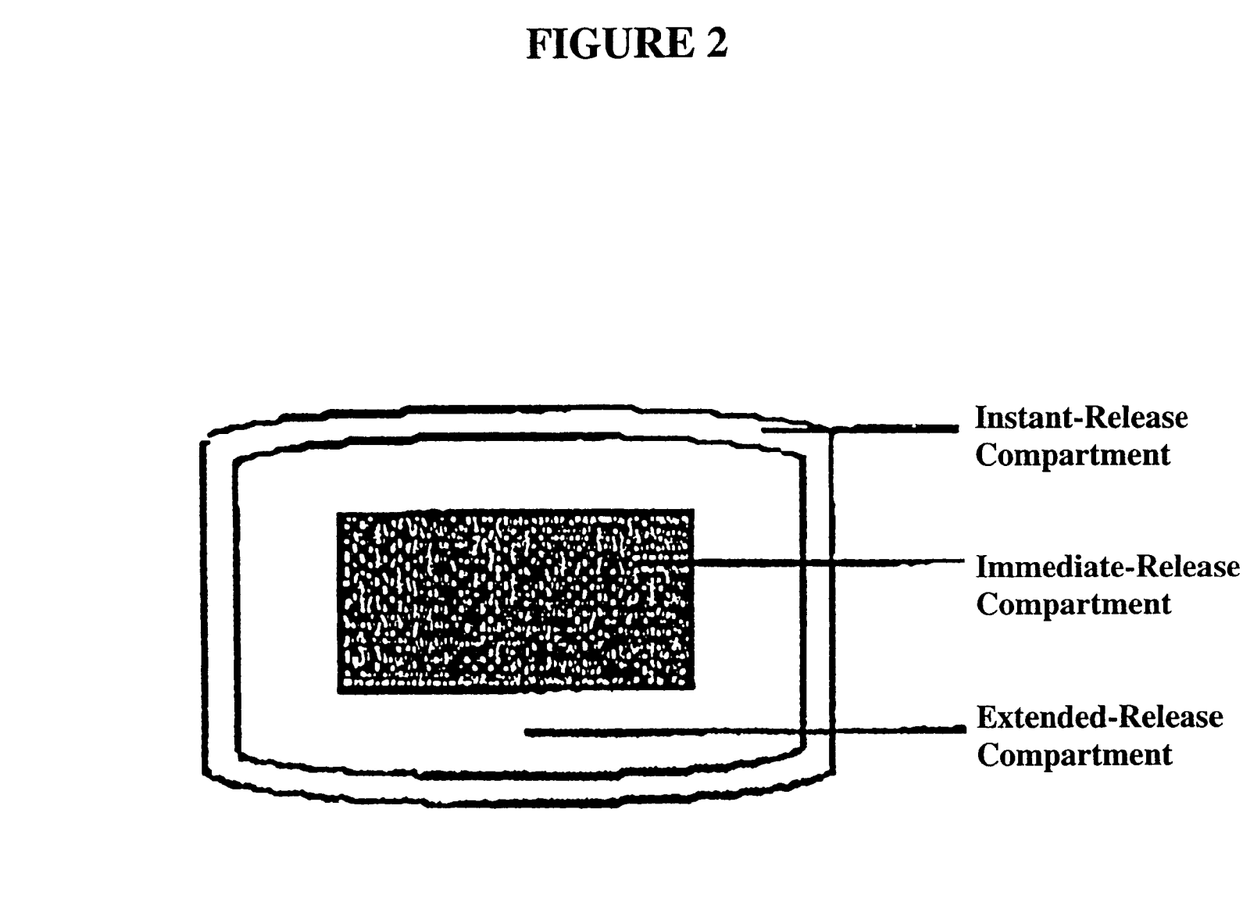
FIG. 2 is a schematic of a press coated, pulsatile drug delivery system of the present invention suitable for oral administration with an immediate-release compartment, which contains a compressed blend of an active agent and one or more polymers, substantially enveloped by an extended-release compartment, which contains a compressed blend of the active agent and hydrophilic and hydrophobic polymers, and substantially enveloped by an instant-release compartment.
Figure 3:
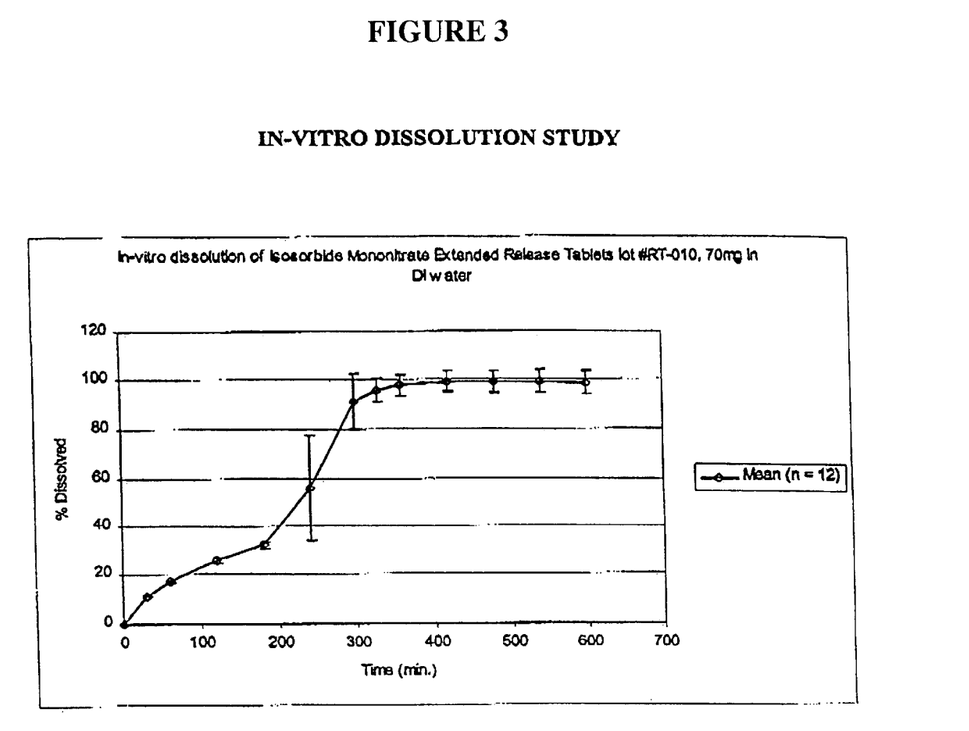
FIG. 3 is a graph showing the in vitro dissolution profile (% dissolved versus time) of isosorbide mononitrate extended release tablets, according to an embodiment of the present invention, in deionized water using a type 2 dissolution apparatus (paddle method) at 37±0.5° C. at 75 rotations per minute (rpm). See U.S. Pharmacopeia XXII <711> Dissolution. The graph reflects the following data.
Figure 4:
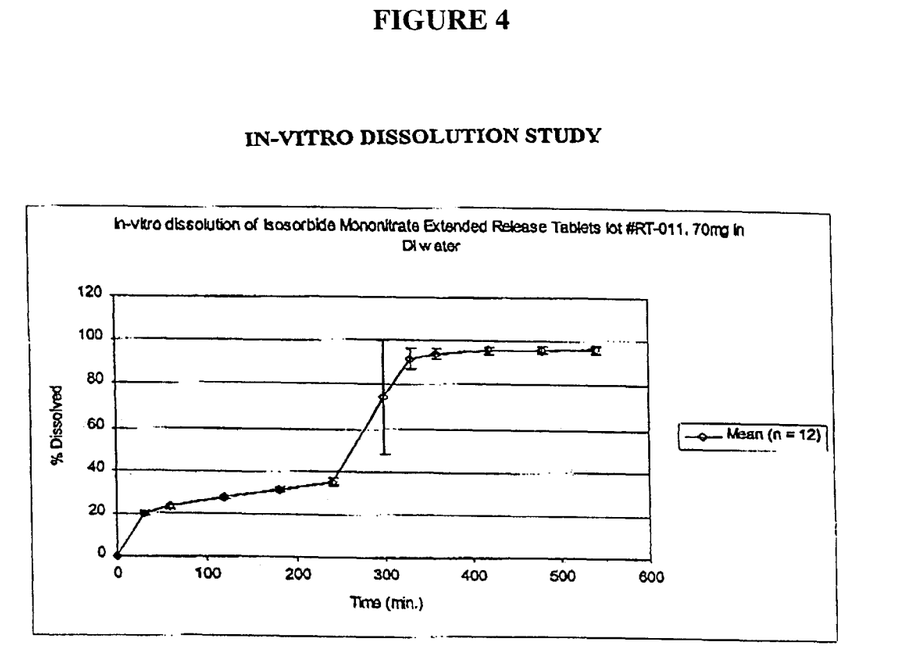
FIG. 4 is a graph showing the in vitro dissolution profile (% dissolved versus time) of isosorbide mononitrate extended release tablets, according to an embodiment of the present invention, in deionized water using USP paddle method at 75 rpm graph reflects the following data.

In accordance with the present invention, the term "active agent" includes one or more drugs, their pharmaceutically acceptable salts, pro-drug forms, metabolites, and derivatives.

Active agents include therapeutic or prophylactic compounds as described in the Physicians' Desk Reference, most preferably including (but not limited to) those prescribed for the prevention and/or treatment of angina and hypertension: dilitiazem, trapidil, urapidil, benziodarone, dipyridamole, isosorbide mononitrate, and lidoflazine; and those prescribed for the prevention and/or treatment of rheumatic diseases such as rheumatoid arthritis: non-steroidal antiinflammatory drugs (NSAIDs) and steroidal antiinflammatory drugs such as diclofenac sodium, ibuprofen, ketoprofen, diflunisal, piroxicam, motrin, and naproxin, and combinations thereof.

The active agent of the present invention also preferably includes drugs that are subject to the pass effect. Various examples of such drugs include (but are not limited to) acetaminophen, aldosterone, alprenolol, amitryptyline, aspirin, beclomethasone, diproprionate, bromocriptine, butorphanol tartrate, chlormethiazole, chlorpheniramine, chlorpromazine HCl, cimetidine, codeine, cortisone, cyclobenzamine HCl, desmethylimipramine, dextropropoxyphene, dihydroergotamine, diltiazem HCl, dobutamine HCl, domperidone, dopamine HCl, doxepin HCl, epinephrine, ergoloid mesylates, ergotamine tartrate estradiol, ethinylestradiol, flunisolide, fluorouracil, flurazepam HCl, 5-fluoro-21-deoxyuridine, furosemide, glipizide, glyburide, glyceryl trinitrate, guanethidine sulfate, hydralazine HCl, imipramine HCl, indoramin, isoethorine HCl, isoethrine mesylate, isoprenaline, isoproterenol sulfate, isosorbide dinitrate, levallorphan tartrate, levodopa, lidocaine HCl, lignocaine, lorcainide, meperidine HCl, 6-mercaptopurine, metaproterenol sulfate, methoxamine HCl, methylphenidate, methylpreonisolone, methyltestosterone mesylate, metoclopramide, metoprolol tartrate, morphine sulfate, nalbuphine HCl, naloxone HCl, neostigmine, nifedipine, nitrendipine, nitroglycerin, norepinephrine bitartrate, norethindrone, nortriptylene HCl, oxprenolol, oxyphenbutazone, penicillamine, pentazocine HCl, pentazocine lactate, pentobarbital, petnidine, phenacetin, phentolamine HCl, phentolamine mesylate, phenylephrine HCl, phenylephrine bitartrate, phenytoin, pindolal, prazosin, prednisone, progesterone, propoxyphene HCl, propoxyphene napsylate, propranolol HCl, quinidine, reserpine, ritodrine HCl, salicylamide, salbutamol, secobarbital, testosterone, terbutaline, timolol maleate, tolbutamide, and verapamil HCl.

In a preferred embodiment of the present invention, the active agent may include the drug, isosorbide-5-mononitrate, an organic nitrate, which is a vasodilator with effects on both arteries and veins. The empirical formula is $C_6H_9NO_6$ and the molecular weight is 191.14. The chemical name for isosorbide mononitrate is 1,4:3,6-dianhydro-D-glucitrol 5-nitrate.

Isosorbide mononitrate is the major active metabolite of isosorbide dinitrate and most of the clinical activity of the dinitrate can be attributable to the mononitrate. A principal pharmacological action of isosorbide mononitrate is relaxation of vascular smooth muscle and consequent dilatation of peripheral arteries and veins, especially the latter. Dilatation of the veins is known to promote peripheral pooling of blood and decrease venous return to the heart, thereby reducing left ventricular and-diastolic pressure and pulmonary capillary wedge pressure (preload). Arteriolar relaxation reduces systemic vascular resistance, systolic arterial pressure, and mean arterial pressure (afterload). Dilation of the coronary arteries also occurs. The relative importance of preload reduction, afterload reduction, and coronary dilatation remains undefined. The mechanism by which isosorbide mononitrate relieves angina pecteria is not fully understood.

Isosorbide mononitrate is rapidly and completely absorbed from the gastrointestinal tract. In humans, isosorbide mononitrate is not subject to first pass metabolism in the liver. The overall elimination half-life of isosorbide mononitrate is about 6 hours. The rate of clearance is the same in healthy young adults, and in patients with various degrees of renal, hepatic, or cardiac dysfunction.

In accordance with the present invention, the term "polymer" includes single or multiple polymeric substances, which can swell, gel, degrade or erode on contact with an aqueous environment (e.g., water), such as one or more of alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polacrilin potassium, powdered cellulose, pregelatinized starch, sodium alginate, sodium starch glycolate, starch, ethylcellulose, gelatin, hydroxyethyl cellulose, hydroxypropyl cellulose, hydroxypropyl methylcellulose, polymethacrylates, povidone, pregelatinized starch, shellac, and zein, and combinations thereof.

The "hydrophilic polymers" of the present invention include one or more of carboxymethylcellulose, natural gums such as guar gum or gum acacia, gum tragacanth, or gum xanthan, hydroxyethyl cellulose, hydroxypropyl cellulose, hydroxypropyl methylcellulose, methylcellulose, and povidone. "Hydrophilic polymers" also include sodium carboxymethycellulose, hydroxymethyl cellulose, polyethelene oxide, hydroxyethyl methyl cellulose, carboxypolymethylene, polyethelene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), an alkali metal or alkaline earth metal, carageenate alginates, ammonium alginate, sodium alganate, or mixtures thereof.

The "hydrophobic polymers" of the present invention include one or more of carbomer, carnauba wax, ethylcellulose, glyceryl palmitostearate, hydrogenated castor oil, hydrogenated vegetable oil type 1, microcrystalline wax, polacrilin potassium, polymethacrylates, stearic acid, a pharmaceutically acceptable acrylic polymer, including, but not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly (methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH dependent.

For purposes of the present invention, the term "extended release" is intended to define a compartment with a dissolution profile in which the active agent or drug is dissolved in the following manner: 5–40% in the first hour, 20–75% within three hours, 40–95% within six hours, and not less than 60% within eight hours, based on the amount of drug in the compartment. Furthermore, the dissolution profile is generated from the use of a type 2 dissolution apparatus (paddle) according to U.S. Pharmacopeia XXII at 37° C.±0.5° C. in deionized water at 75 rotations per minute.

The term "immediate release" is intended to define a compartment with a dissolution profile in which the active agent or drug is dissolved in the following manner: 10–75% within one hour and no less than 90% within six hours, based on the amount of drug in the compartment. Furthermore, the dissolution profile is generated from the use of a type 2 dissolution apparatus (paddle) according to U.S. Pharmacopeia XXII at 37° C.±0.5° C. in deionized water at 75 rotations per minute.

"Instant release" means a compartment with a dissolution profile in which the active agent or drug is dissolved in the following manner: at least 80% within 15 minutes and no less than 95% within one hour, based on the amount of drug in the compartment. Furthermore, the dissolution profile is generated from the use of a type 2 dissolution apparatus (paddle) according to U.S. Pharmacopeia XXII at 37° C.±0.5° C. in deionized water at 75 rotations per minute.

The term "substantially envelop" is intended to define the total or near-total enclosure of a compartment. Such an enclosure includes, preferably, at least 80% enclosure, more preferably at least 90% enclosure, and most preferably at least 95% enclosure.

The term "pulsed" when used in conjunction with the release of the active agent or drug is intended to define an action by a carrier of an active agent or drug in which the continuing release of the active agent or drug is temporarily increased by an infusion of active agent or drug characterized by an increase of 10–500%, preferably 20–300%, most preferably, 35–100%, of active agent or drug released from the dosage form. Such an increase is characterized by a 0.00001 to 500 mg per hour increase in release as compared to the release rate before the pulse.

The term "interrupted" when used in conjunction with the release of the active agent or drug is intended to mean the addition of a second and different release rate of active agent to the initial or first release rate which the present drug formulation undergoes upon introduction to a patient. The first release rate may terminate with the interruption. Preferably, the first release rate does not stop with the interruption, but continues during at least a portion of the interruption period. Most preferably, the first release rate continues throughout the interruption period.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

Example 1

The method below was employed to obtain a press coated, pulsatile drug delivery system, the composition of which is set forth in the tables immediately following:

Immediate-Release Compartment. Isosorbide mononitrate was first mixed with silicon dioxide in a Patterson-Kelley V-blender for 10 minutes, then microcrystalline cellulose and croscarmellulose sodium were added and blended for 10 more minutes. Finally, magnesium stearate was added to the blender and mix for another 10 minutes. The powder blend was then compressed using a Manesty Dry-cota with 0.2031" in diameter, round, flat-face punch and die set. The hardness of the tablets were maintained at 4±2 kp.

Immediate-Release Compartment Plus Extended-Release Compartment Isosorbide mononitrate was first mixed with silicon dioxide in a Patterson-Kelley V-blender for 10 minutes, then hydroxypropyl methylcellulose 2208 and microcrystalline cellulose were added and blended for 10 more minutes. Finally, hydrogenated vegetable oil and magnesium stearate were added to the blender and mix for another 10 minutes. The core tablets were press-coated using the Manesty Dry-cota with 0.3600"in diameter, round, shallow concave punch and die set. The hardness of the tablets were maintained at 12±4 kp.

Example 2

Immediate-Release Compartment Plus Extended-Release Compartment Plus Instant-Release Compartment. The method of manufacture for the extended-release tablets is the same as described in Example 1. The application of the instant-release compartment was done by charging the extended-release tablets into a perforated pan coater or a fluidized particle coater and coated with a solution consist of isosorbide-5-mononitrate 80% w/ lactose and hydroxypropyl methylcellulose type 2910. The instant release coating may also be applied using the press-coating process described in Example 1 above with a blend consisting of isosorbide-5-mononitrate 80% w/ lactose and hydroxypropyl methylcellulose type 2910.

In addition, the formulation of respective release compartments can occur by appropriate granulation methods. In wet granulation, solutions of the binding agent (polymer) are added with stirring to the mixed powders. The powder mass is wetted with the binding solution until the mass has the consistency of damp snow or brown sugar. The wet granulated material is forced through a sieving device. Moist material from the milling step is dried by placing it in a temperature controlled container. After drying, the granulated material is reduced in particle size by passing through a sieving device. Lubricant is added, and the final blend is then compressed.

In fluid-bed granulation, particles of inert material and/or active agent are suspended in a vertical column with a rising air stream. While the particles are suspended, the common granulating materials in solution are sprayed into the column. There is a gradual particle buildup under a controlled set of conditions resulting in tablet granulation. Following drying and the addition of lubricant, the granulated material is ready for compression.

In dry-granulation, the active agent, diluent, and lubricant are blended and compressed into large tablets. The compressed large tablets are comminuted through the desirable mesh screen by sieving equipment. Some more lubricant is added to the granulated material and blended gently. The material is then compressed into tablets.

TABLE 1

| | Quantity/Tablet | |
|---|---|---|
| | Example #1 RT-010 (press-coated w/o instant-release coating) | Example #2 RT-01 1 (press coated w/ instant-release coating) |
| Immediate-Release (IR) Compartment | | |
| Isosorbide-5-mononitrate 80% w/ lactose | 50.0 mg | 50.0 mg |
| Croscarmellose sodium | 1.6 mg | 1.6 mg |
| Microcrystalline cellulose | 26.8 mg | 26.8 mg |
| Colloidal silicon dioxide | 0.8 mg | 0.8 mg |
| Magnesium stearate | 0.8 mg | 0.8 mg |

TABLE 1-continued

|  | Quantity/Tablet | |
| --- | --- | --- |
|  | Example #1 RT-010 (press-coated w/o instant-release coating) | Example #2 RT-011 (press coated w/ instant-release coating) |
| Total: IR Compartment Plus Extended-Release (ER) Compartment | 80.0 mg | 80.0 mg |
| IR Compartment | 80.0 mg | 80.0 mg |
| Isosorbide-5-mononitrate 80% w/lactose | 37.5 mg | 18.8 mg |
| Hydroxypropyl methylcellulose type 2208 | 61.6 mg | 61.6 mg |
| Microcrystalline cellulose | 70.3 mg | 89.0 mg |
| Hydrogenated vegetable oil type 1 | 46.2 mg | 46.2 mg |
| Colloidal silicon dioxide | 2.2 mg | 2.2 mg |
| Magnesium stearate | 2.2 mg | 2.2 mg |
| Total: IR Compartment Plus ER Compartment Plus Instant-Release Compartment | 300.0 mg | 300.00 mg |
| IR Compartment Plus ER Compartment |  | 300.0 mg |
| Isosorbide-5-mononitrate 80% w/lactose |  | 18.7 mg |
| Hydroxypropyl methylcellulose type 2910 |  | 1.9 mg |
| Total: |  | 320.6 mg |

TABLE 2

EXCIPIENT RANGE

|  | Quantity/tablet Example #1 RT-010 (press coated w/o instant-release coating) | Percent | Range |
| --- | --- | --- | --- |
| Immediate-Release Compartment |  |  |  |
| Isosorbide-5-mononitrate 80% w/lactose | 50.0 mg | 62.5% |  |
| Croscarmellose sodium | 1.6 mg | 2.0% | 0.5–10.0% |
| Microcrystalline cellulose | 26.8 mg | 33.5% | 18.0–36.0% |
| Colloidal silicon dioxide | 0.8 mg | 1.0% | 0.5–2.0% |
| Magnesium stearate | 0.8 mg | 1.0% | 0.5–2.0% |
| Total: | 80.0 mg |  |  |
| Extended-Release Compartment |  |  |  |
| Isosorbide-5-mononitrate 80% w/lactose | 37.5 mg | 17.0% |  |
| Hydroxypropyl methylcellulose type 2208 | 61.6 mg | 28.0% | 15.0–40.0% |
| Microcrystalline cellulose | 70.3 mg | 32.0% | 8.0–57.0% |
| Hydrogenated vegetable oil type 1 | 46.2 mg | 21.0% | 10.0–30.0% |
| Colloidal silicon dioxide | 2.2 mg | 1.0% | 0.5–2.0% |
| Magnesium stearate | 2.2 mg | 1.0% | 0.5–2.0% |
| Total: | 220.0 mg |  |  |

All aforementioned patents, patent applications and publications are herein incorporated by reference in their entirety as though set forth in full.

The invention has been disclosed broadly and illustrated in reference to representative embodiments described above. Those skilled in the art will recognize that various modifications can be made to the present invention without departing from the spirit and scope thereof.

We claim:

1. A press-coated tablet suitable for oral administration, comprising:
   (a) an immediate-release compartment comprising a compressed blend of an active agent and one or more polymers, wherein said immediate release compartment is characterized by a dissolution profile in which 10–75% of the active agent is dissolved within one hour and not less than 90% of the active agent is dissolved within 6 hours, based on the total amount of the active agent in the compartment, wherein the dissolution profile is measured in a type 2 dissolution apparatus (paddle) according to U.S. Pharmacopeia XXII at 37° C.±0.5° C. in deionized water at 75 rotations per minute, and
   (b) an extended-release compartment, wherein said extended-release compartment is characterized by a dissolution profile in which 5–40% of the active agent is dissolved within one hour, 20–75% of the active agent is dissolved within three hours, 40–95% of the active agent is dissolved within 6 hours, and not less than 60% of the active agent is dissolved within 8 hours, based on the total amount of the active agent in the compartment, wherein the dissolution profile is measured in a type 2 dissolution apparatus (paddle) according to U.S. Pharmacopeia XXII at 37° C.±0.5° C. in deionized water at 75 rotations per minute, wherein the extended-release compartment is formed by press-coating to substantially envelop the immediate-release compartment, and comprises a compressed blend of the active agent, a hydrophilic polymer and hydrophobic material,
wherein the tablet exhibits a first order release of the active agent interrupted by a pulsed delivery of the active agent.

2. The tablet of claim 1, further comprising
   (c) an instant-release compartment, characterized by a dissolution profile in which at least 80% of the active agent is dissolved within 15 minutes, based on the total amount of the active agent in the compartment, wherein the dissolution profile is measured in a type 2 dissolution apparatus (paddle) according to U.S. Pharmacopeia XXII at 37° C. 0.5° C. in deionized water at 75 rotations per minute, wherein the instant release compartment is formed by coating to substantially envelop the extended-release compartment, and comprises a compressed blend of an active agent and one or more polymers, and wherein the instant-release compartment provides a release of the active agent before the first order release.

3. The tablet of claim 2, wherein the instant-release compartment is formed by film coating.

4. The tablet of claim 1, wherein the active agent is a drug, or a pharmaceutically acceptable salt thereof.

5. The tablet of claim 4, wherein the drug is a therapeutic drug.

6. The tablet of claim 4, wherein the drug is a prophylactic drug.

7. The tablet of claim 4, wherein the drug is selected from the group consisting of diltiazem, trapidil, urapidil, benziodarone, dipyridamole, isosorbide mononitrate and lidoflazine.

8. The tablet of claim 4, wherein the drug is selected from the group consisting of a non-steroidal anti-inflammatory drug and a steroidal anti-inflammatory drug.

9. The tablet of claim 4, wherein the drug is selected from the group consisting of acetaminophen, aldosterone, alprenolol, amitryptyline, aspirin, beclomethasone, diproprionate, bromocriptine, butorphanol tartrate, chlormethiazole, chlorpheniramine, chlorpromazine HCl, cimetidine, codeine, cortisone, cyclobenzamine HCl, desmethylimipramine, dextropropoxyphene, dihydroergotamine, diltiazem HCl, dobutamine HCl, domperidone, dopamine HCl, doxepin HCl, epinephrine, ergoloid mesylates, ergotamine tartrate estradiol, ethinylestradiol, flunisolide, fluorouracil, flurazepam HCl, 5-fluoro-21-deoxyuridine, furosemide, glipizide, glyburide, glyceryl trinitrate, guanethidine sulfate, hydralazine HCl, imipramine HCl, indoramin, isoethorine HCl, isoethrine mesylate, isoprenaline, isoproterenol sulfate, isosorbide dinitrate, levallorphan tartrate, levodopa, lidocaine HCl, lignocaine, lorcainide, meperidine HCl, 6-mercaptopurine, metaproterenol sulfate, methoxamine HCl, methylphenidate, methylpreonisolone, methyltestosterone mesylate, metoclopramide, metoprolol tartrate, morphine sulfate, nalbuphine HCl, naloxone HCl, neostigmine, nifedipine, nitrendipine, nitroglycerin, norepinephrine bitartrate, norethindrone, nortriptylene HCl, oxprenolol, oxyphenbutazone, penicillamine, pentazocine HCl, pentazocine lactate, pentobarbital, petnidine, phenacetin, phentolamine HCl, phentolamine mesylate, phenylephrine HCl, phenylephrine bitartrate, phenytoin, pindolal, prazosin, prednisone, progesterone, propoxyphene HCl, propoxyphene napsylate, propranolol HCl, quinidine, reserpine, ritodrine HCl, salicylamide, salbutamol, secobarbital, testosterone, terbutaline, timolol maleate, tolbutamide, and verapamil HCl.

10. The tablet of claim 4, wherein the drug is isosorbide-5-mononitrate.

11. The tablet of claim 1, wherein the active agent exhibits the following in vitro dissolution profile when measured in a type 2 dissolution apparatus (paddle) according to U.S. Pharmacopeia XXII at 37° C.±0.5° C. in deionized water at 75 rotations per minute:

from about 0% to about 90% of the active agent is released between 1 hour and 16 hours of measurement in the apparatus; and from about 0% to about 100% of the active agent is released between 1.5 hours and 28 hours of measurement in the apparatus.

12. The tablet of claim 1, wherein the active agent exhibits the following in vitro dissolution profile when measured in a type 2 dissolution apparatus (paddle) according to U.S. Pharmacopeia XXII at 37° C.±0.5° C. in deionized water at 75 rotations per minute:

from about 10% to about 75% of the active agent is released between 1 hour and 5 hours of measurement in the apparatus; and not less than 90% of the active agent is released after 6 hours of measurement in the apparatus.

13. The tablet of claim 1, wherein the active agent exhibits the following in vitro dissolution profile when measured in a type 2 dissolution apparatus (paddle) according to U.S. Pharmacopeia XXII at 37° C.±0.5° C. in deionized water at 75 rotations per minute:

from about 0% to about 50% of the active agent is released after 1 hour of measurement in the apparatus;

from about 0% to about 90% of the active agent is released between 1 hour and 16 hours of measurement in the apparatus; and from about 0% to about 100% of the active agent is released between 1.5 hours and 28 hours of measurement in the apparatus.

14. The tablet of claim 1, wherein the active agent exhibits the following in vitro dissolution profile when measured in a type 2 dissolution apparatus (paddle) according to U.S. Pharmacopeia XXII at 37° C.±0.5° C. in deionized water at 75 rotations per minute:

from about 0% to about 35% of the active agent is released after 1 hour of measurement in the apparatus;

from about 10% to about 90% of the active agent is released between 1 hour and 5 hours of measurement in the apparatus; and no less than 90% of the active agent is released after 6 hours of measurement in the apparatus.

15. The tablet of claim 1, wherein the one or more polymers are selected from the group consisting of alginic acid, carboxymethylcellulose calcium, carboxymethylcellulose sodium, colloidal silicon dioxide, croscarmellose sodium, crospovidone, guar gum, magnesium aluminum silicate, magnesium stearate, methylcellulose, microcrystalline cellulose, polacrilin potassium, powdered cellulose, pregelatinized starch, sodium alginate, sodium starch glycolate, starch, ethylcellulose, gelatin, hydroxyethyl cellulose, hydroxypropyl cellulose, hydroxypropylmethyl cellulose, polymethacrylate, povidone, shellac and zein.

16. The tablet of claim 15, wherein the one or more polymers are selected from the group consisting of colloidal silicon dioxide, croscarmellose sodium, magnesium stearate, microcrystalline cellulose and hydroxypropylmethyl cellulose.

17. The tablet of claim 1, wherein the hydrophilic polymer is at least one member selected from the group consisting of carboxymethylcellulose, guar gum, gum acacia, gum tragacanth, gum xanthan, hydroxyethyl cellulose, hydroxypropyl cellulose, hydroxypropylmethyl cellulose, methylcellulose, povidone, sodium carboxymethycellulose, hydroxymethyl cellulose, polyethelene oxide, hydroxyethyl methyl cellulose, carboxypolymethylene, polyethelene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), an alkali metal, alkaline earth metal, carageenate alginates, ammonium alginate, sodium alganate.

18. The tablet of claim 17, wherein the hydrophilic polymer comprises hydroxypropylmethyl cellulose.

19. The tablet of claim 1, wherein the hydrophobic material is at least one member selected from the group consisting of carbomer, carnauba wax, ethylcellulose, glyceryl palmitostearate, hydrogenated castor oil, hydrogenated vegetable oil, microcrystalline wax, polacrilin potassium, polymethacrylate, stearic acid, a pharmaceutically acceptable acrylic polymer, including, but not limited to acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolyer, poly(methyl methacrylate), poly(methyl methacrylate) copolymer, polyacrylamide, aminoalkyl methacrylate copolymer, poly(methacrylic acid anhydride), and glycidyl methacrylate copolymers.

20. The tablet of claim 19, wherein the hydrophobic material comprises hydrogenated vegetable oil.

* * * * *